US012758507B2

(12) United States Patent
Yang et al.

(10) Patent No.: US 12,758,507 B2
(45) Date of Patent: Oct. 13, 2026

(54) METHOD FOR PREPARING DRUG-LOADED SILK FIBROIN NANOCAPSULE, AND PRODUCT THEREOF

(71) Applicant: ZHEJIANG UNIVERSITY, Hangzhou (CN)

(72) Inventors: Mingying Yang, Hangzhou (CN); Jie Wang, Hangzhou (CN); Yuyin Chen, Hangzhou (CN)

(73) Assignee: ZHEJIANG UNIVERSITY, Hangzhou (CN)

(*) Notice: Subject to any disclaimer, the term of this patent is extended or adjusted under 35 U.S.C. 154(b) by 1025 days.

(21) Appl. No.: 17/622,759

(22) PCT Filed: Jun. 23, 2020

(86) PCT No.: PCT/CN2020/097676
§ 371 (c)(1),
(2) Date: Dec. 24, 2021

(87) PCT Pub. No.: WO2020/259487
PCT Pub. Date: Dec. 30, 2020

(65) Prior Publication Data

US 2022/0273580 A1 Sep. 1, 2022

(30) Foreign Application Priority Data

Jun. 26, 2019 (CN) ......................... 201910558742.9

(51) Int. Cl.
*A61K 9/51* (2006.01)
*A61K 31/704* (2006.01)

(52) U.S. Cl.
CPC .......... *A61K 9/5169* (2013.01); *A61K 9/5192* (2013.01); *A61K 31/704* (2013.01)

(58) Field of Classification Search
CPC .................................................. A61K 9/5169
See application file for complete search history.

(56) References Cited

U.S. PATENT DOCUMENTS 7,101,575 B2 * 9/2006 Donath .................... B01J 13/02 424/489
2018/0104664 A1* 4/2018 Fernandez ........... B01J 19/0046

FOREIGN PATENT DOCUMENTS

CN 110327307 A 10/2019
WO WO-2006037160 A1 * 4/2006 ............... B32B 9/02
(Continued)

OTHER PUBLICATIONS

Merriam-Webster "microcapsules" https://www.merriam-webster.com/dictionary/microsphere, no pagination, no date. accessed Nov. 12, 2024.*

(Continued)

*Primary Examiner* — Carlos A Azpuru
(74) *Attorney, Agent, or Firm* — Getech Law LLC; Jun Ye

(57) ABSTRACT

The present invention discloses a method for preparing a drug-loaded silk fibroin nanocapsule, and a prepared drug-loaded silk fibroin nanocapsule. The method comprises: performing a coating treatment of applying alternating layers of silk fibroin and 3-aminopropyl triethoxysilane on functionally modified polystyrene microspheres, to ultimately obtain a multi-layer-structured coated polystyrene composite with a negative or positive potential, and finally removing the functionally modified polystyrene template with a template-removing reagent, to obtain a drug-loaded silk fibroin nanocapsule. The functionally modified polystyrene microspheres are positive potential microspheres, and silk fibroin is used for the first coating. In the case of negative potential microspheres, 3-aminopropyl triethoxysilane is used for the first treatment. The process is simple and has wide applicability. The dimensions of the prepared microcapsule can be controlled at the nanometer level, so (Continued)

that the microcapsule can more effectively transport a drug to the interior of a cell to come into play.

8 Claims, 2 Drawing Sheets

(56) References Cited

FOREIGN PATENT DOCUMENTS

| | | | | | |
|---|---|---|---|---|---|
| WO | 2010059963 | | * | 5/2010 | |
| WO | WO-2013151670 | A2 | * | 10/2013 | ......... A61K 31/7088 |

OTHER PUBLICATIONS

Correa et al. (Adv. Funct. Mater. 2016, 26(7) 991-1003).*
CN201910558742.9- First Office Action mailed on Mar. 17, 2020, 9 pages.
CN201910558742.9- Notice of Grant mailed on May 6, 2020, 4 pages.
PCT /CN2020/097676- International Search Report and Written opinion mailed on Sep. 25, 2020, 17 pages.

* cited by examiner

METHOD FOR PREPARING DRUG-LOADED SILK FIBROIN NANOCAPSULE, AND PRODUCT THEREOF

CROSS REFERENCE TO RELATED APPLICATIONS

This application is a 371 of International Application No. PCT/CN2020/097676, filed Jun. 23, 2020, which claims priority to foreign application, Chinese Application No. 201910558742.9, filed Jun. 26, 2019. The contents of each of the above-captioned patent applications are hereby expressly incorporated herein by reference in their entireties.

TECHNICAL FIELD

The present invention belongs to the technical field of biology, and particularly relates to a method for preparing a drug-loaded silk fibroin nanocapsule and a product thereof.

BACKGROUND

Silk fibroin is a kind of natural high-molecular polymer, and has good biocompatibility, high plasticity and excellent mechanical properties, and is extensively studied and applied in the fields of bone tissue engineering and drug carriers. In the field of drug carrier, the most common way of silk fibroin is microspheres; the preparation methods of fibroin microspheres are diversified and process is simple; for example, Chinese patent literature (publication date: Sep. 30, 2015 and publication No.: CN103341175B) discloses a method for preparing a fibroin microsphere. However, as a drug carrier, fibroin microspheres have limitations; The drug-loading way of silk microspheres is too single, and most of them depend on a specific surface area for physical absorption, and thus the drug loading capacity is limited, and in vivo transportation process will also cause drug loss. Therefore, a novel silk fibroin material form is urgently needed for designing a drug carrier, that can efficiently improve the drug loading.

A hollow fibroin microsphere or hollow microcapsule can provide huge drug loading space with its internal hollow structure, and its outer layer structure can protect the drug administration more effectively and thus, is concerned widely. At present, the method for preparing a fibroin microcapsule still gives priority to the layer-by-layer self-assembly technology; an organic or inorganic substance is used as a soft/hard template to alternatively deposit layers of silk fibroin by weak interaction (such as, electrostatic attraction, hydrogen bond, and coordinate bond), thus forming molecular aggregates after through multiple repetitions, and finally, the template is removed to obtain a hollow silk fibroin microcapsule. However, due to the instability of the silk fibroin structure, during self-assembly, silk fibroin is always subjected to be transformed into β-sheet secondary structure by organic solvent for stabilizing the structure, which increases the complexity of the operation, on the other hand, it easily causes the residual of organic solvent. The surface potential on silk fibroin shows weak electronegativity, and thus usually needs to be subjected to charge modification, thereby achieving good electrostatic adsorption effect. Moreover, the fibroin microcapsule prepared currently is micron-sized and thus, hardly gets into cells for effective drug delivery, and in vivo circulation is also blocked as well. Therefore, to sum up, there is no self-assembly method with simple process at present to overcome the above technical shortcomings, thus preparing a hollow nanoscale fibroin microcapsule as a drug carrier for effective drug delivery.

SUMMARY

To overcome the shortcomings in the preparation technology of fibroin microcapsules, such as, complex process, large microcapsule size, the present invention provides a method for preparing a drug-loaded silk fibroin nanocapsule. The method is simple and rapid and has strong applicability, and high preparation efficiency.

To achieve the above objective, the technical solution provided by the present invention is as follows:

a method for preparing a drug-loaded silk fibroin nanocapsule includes the following steps: performing a coating treatment of applying alternating layers of silk fibroin and 3-aminopropyl triethoxysilane on functionally modified polystyrene microspheres, to ultimately obtain a multi-layer-structured coated polystyrene composite with a negative or positive potential, and finally removing the functionally modified polystyrene template with a template-removing reagent, to obtain a drug-loaded silk fibroin nanocapsule; where, the functionally modified polystyrene microspheres are positive potential microspheres, and silk fibroin is used for the first coating; and in the case of negative potential microspheres, 3-aminopropyl triethoxysilane is used for the first treatment.

Preferably, the functionally polystyrene microspheres was modified with an amination positive potential or a carboxylation negative potential, and the polystyrene microspheres have a diameter of 0.05-0.5 μm, further preferably, 0.05-2 μm. For example, a commercially available amino polystyrene microsphere or carboxyl polystyrene microsphere product may be used directly; the commercially available amino polystyrene microsphere or carboxyl polystyrene microsphere is generally kept in the form of aqueous solution, and the mass percent concentration is generally within 2-6%.

Preferably, the step of performing a coating treatment by silk fibroin is as follows: placing the to-be-coated polystyrene microspheres in a silk fibroin aqueous solution to be dispersed evenly, then putting the dispersed solution at 0-10° C. for continuous reaction for 5-50 min to complete the coating, where the silk fibroin aqueous solution has a concentration of 1-10 mg/mL.

In the step of performing a coating treatment by silk fibroin, the to-be-coated polystyrene microspheres include functionally modified polystyrene microspheres which are not coated any material and have a positive potential on the original surfaces, and it can also be polystyrene microspheres which are alternatively coated with silk fibroin and 3-aminopropyl triethoxysilane for once or multiple times, and the final treatment is coated with 3-aminopropyl triethoxysilane.

When silk fibroin is coated, the system may be homogenized by blowing or/and ultrasonic dispersion. After silk fibroin coating, solvent may be not separated, and the coating of the subsequent aminopropyl triethoxysilane (3-aminopropyl triethoxysilane) may be performed directly.

Preferably, the step of performing a coating treatment by 3-aminopropyl triethoxysilane is as follows: mixing the to-be-coated polystyrene microspheres with 3-aminopropyl triethoxysilane in a solvent evenly, and then putting the mixed solution at 0-10° C. for continuous reaction for 5-50 min to complete the reaction, and removing the solvent to complete the coating.

In the step of performing a coating treatment by 3-aminopropyl triethoxysilane, the to-be-coated polystyrene microspheres include functionally modified polystyrene microspheres which are not coated any material and have a negative potential on the original surfaces, and also polystyrene microspheres which are alternatively coated with silk fibroin and 3-aminopropyl triethoxysilane for once or multiple times, and the final treatment is coated with silk fibroin.

After being coated with 3-aminopropyl triethoxysilane, the obtained product is usually centrifuged at 10000-20000 rpm for 10-20 min to separate solvent, and then washed for several times, thus obtaining the 3-aminopropyl triethoxysilane-coated microspheres.

In this present invention, the addition of silk fibroin and 3-aminopropyl triethoxysilane is controlled to ensure that the silk fibroin-coated microsphere has a negative potential on the surface, and the 3-aminopropyl triethoxysilane-treated microsphere has a positive potential on the surface.

In this present invention, for 10 mg functionally modified polystyrene microspheres, the required silk fibroin was 1-20 mg, further preferably 2-8 mg, for each silk fibroin coating treatment; the required 3-aminopropyl triethoxysilane was 1-5 mg, further preferably 1-2 mg for each 3-aminopropyl triethoxysilane coating treatment.

Preferably, silk fibroin is coated once and then 3-aminopropyl triethoxysilane is coated once or 3-aminopropyl triethoxysilane is coated once and then silk fibroin is coated once as a layer, and there are total 3-15 layers. The number of repeats in the step (6) may be 3-12; and each layer thickness of the obtained fibroin microcapsule varies from the different number of self-assembly layers.

As a preferred embodiment, a method for preparing a drug-loaded silk fibroin nanocapsule has the following steps:

(1) extracting silkworm silk fibroin to obtain a silk fibroin aqueous solution, and the concentration of silk fibroin is adjusted to be 1-10 mg/mL;

(2) taking functionally modified polystyrene (polystyrene functionally modified with a positive potential) microspheres as a template, centrifuging and washing to obtain a microsphere precipitate;

(3) blending 5-10 mL silk fibroin solution with polystyrene microspheres (counted by 0.5 mL, 2.5%), and dispersing evenly, and performing ultrasonic treatment, then placing at 0-5° C. for continuous reaction for 10-30 min;

(4) adding 2-5 μL 3-aminopropyl triethoxysilane to the reaction system in the step (3), and shaking vigorously, then placing at 0-5° C. for continuous reaction for 10-30 min;

(5) centrifuging the reaction solution in the step (4) to remove supernatant and washing with deionized water to remove unreacted fibroin and aminopropyl triethoxysilane;

(6) adding silk fibroin once again and repeating the above reaction steps (3)-(5) for 3-12 times—to obtain silk fibroin-coated aggregates with various thickness; and (7) centrifuging the above solution system and treating with a template-removing reagent (e.g., dimethyl formamide) to remove the polystyrene microsphere template, and finally obtaining the drug-loaded silk fibroin nanocapsule.

The invention provide a technical solution concerned the existing shortcomings of complex step and larger size existing in the preparation process of a hollow silk fibroin microcapsule. The present invention includes the following steps successively: extracting silk fibroin to obtain a silk fibroin solution; selecting nano-scaled and surface-modified polystyrene microspheres as a template, adding silk fibroin for coating; and adding 3-aminopropyl triethoxysilane as a cross-linking agent to bind and induce silk fibroin to be coated alternatively, thus forming layer-by-layer assembly; repeating the treatment steps to obtain a microsphere copolymer having a thick and solid silk fibroin shell, then removing the polystyrene microsphere template with dimethyl formamide to obtain a drug-loaded silk fibroin nanocapsule, capable of being used as a drug carrier to load drugs. The process of the present invention is simple and has wide applicability. The dimensions of the prepared microcapsule can be controlled at the nanometer level, so that the microcapsule can more effectively transport a drug to the cell interior to come into play, and the surface potential of the microcapsule can be regulated according to the properties of the drug, thus enhancing electrostatic adsorption and improving the effective drug loading rate.

In this present invention, the added 3-aminopropyl triethoxysilane can be hydrolyzed into silanol compounds, and can be used as a cross-linking agent to perform nucleophilic reaction with hydroxy and carboxyl of silk fibroin, thus forming a copolymer by relying on the binding of hydrogen bonds and electrostatic attraction. At the same time, APTES also provides high positive charges, and can attract negatively charged silk fibroin in the next reaction to induce silk fibroin to be coated, thereby achieving a layer-by-layer self-assembly cycle. Based on the reaction system, the addition of APTES is 2-5 μL.

The present invention further provides a drug-loaded silk fibroin nanocapsule, which is prepared by the prepared method in any of the above technical solutions.

According to drug properties, surface charges on the drug-loaded silk fibroin nanocapsule may be regulated and controlled; and when the final coating treatment is silk fibroin, a microcapsule with a negative potential on the surface may be obtained, which is beneficial to loading positive potential molecule drugs, and when APTES is added finally for coating, a microcapsule with a positive potential on the surface may be obtained, which may load macromolecular drugs with a negative potential, plasmids, DNA and the like. Preferably, when a positive potential molecule drug is loaded, a drug-loaded silk fibroin nanocapsule whose final coating treatment is silk fibroin and surface carries a negative potential is used; when a negative potential molecule drug, a plasmid or DNA is loaded, a drug-loaded silk fibroin nanocapsule whose final coating treatment is 3-aminopropyl triethoxysilane and surface carries a positive potential is used.

Preferably, an antitumor drug with a positive potential is doxorubicin hydrochloride.

With the use of the above technical solutions, compared with the prior art, the present invention has the following distinctive advantages:

(1) different from the existing method that because silk fibroin is coated by means of a hydrogen bond or hydrophilic/hydrophobic force, adsorption capacity is weak and unstable, and silk fibroin needs to be subjected to β-sheet treatment, the present invention introduces APTES both have hydrogen bonds and produce electrostatic attraction, which can make silk fibroin absorbed on the surface of a template more stably. Therefore, β-sheet treatment is not required any longer. The present invention decreases β-sheet treatment on silk fibroin during preparation, which not only simplifies the preparation process, but also relieves the toxic and side effects caused by the β-sheet treatment of an organic solvent.

(2) The present invention introduces aminopropyl triethylsilicane as a crosslinking agent and exerts the non-covalent bond effect of a hydrogen bond and electrostatic attraction for binding, such that the formed silk fibroin can be deposited stably, and it is unnecessary to perform β treatment with an organic solvent every time.

(3) The present invention introduces a nano microsphere template in the preparation technology, thus obtaining a silk fibroin nanocapsule, which can deliver drugs to cells more effectively.

(4) The present invention can determine the positive and negative properties of the potential on the surface of the silk fibroin microcapsule according to the outermost layer coating condition (namely, silk fibroin or APTES).

DETAILED DESCRIPTION OF THE EMBODIMENTS

The present invention will be further described by the following examples, and the following examples are used to explain the present invention, but not construed as limiting the present invention.

Examples of the present invention are as follows:

Example 1

Figure 1:
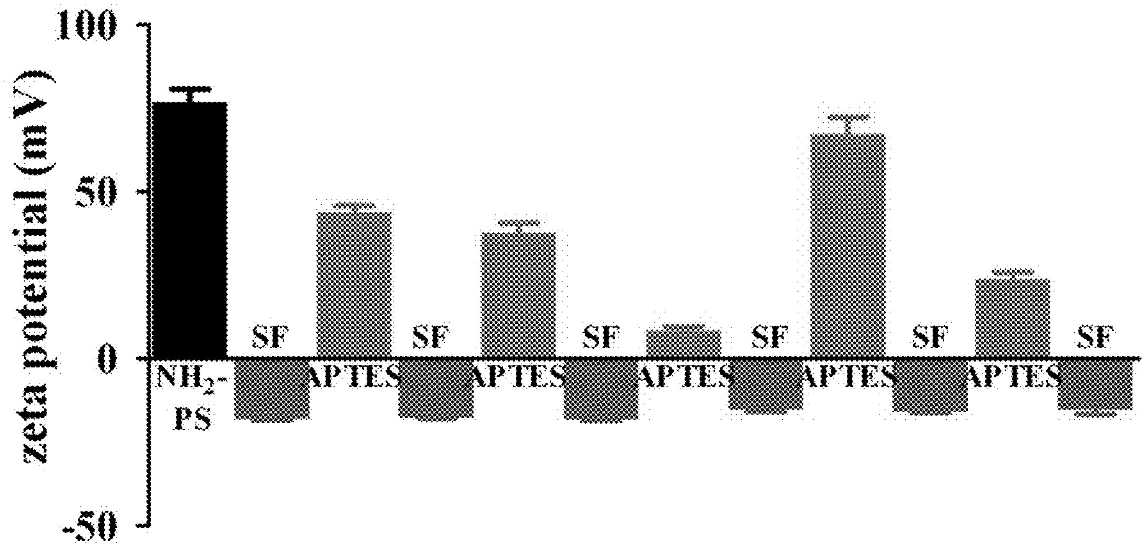
FIG. 1 shows a variation diagram of a surface potential in a preparation process of drug-loaded silk fibroin nanocapsule in Example 1.
Figure 2:
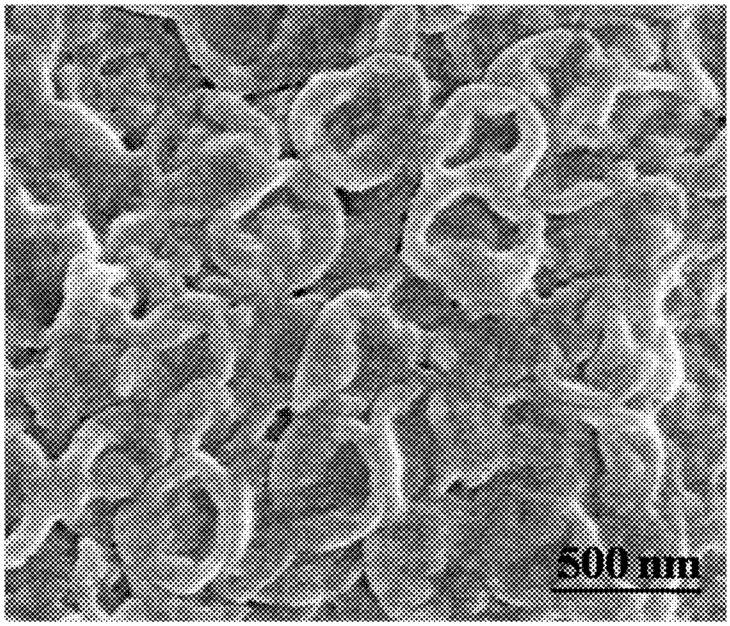
FIG. 2 shows a scanning electron microscope (SEM) diagram of morphology of the drug-loaded silk fibroin nanocapsule prepared in Example 1.

A method for preparing a drug-loaded silk fibroin nanocapsule in this example has the following steps:

(1) silkworm silk fibroin was extracted and a concentration of the silk fibroin was regulated to be 1 mg/mL for further use (solvent was water);

(2) 0.5 mL surface-aminated (—$NH_2$) polystyrene microsphere solution (Aladdin, amino polystyrene microsphere, concentration: 25 g/L, and microsphere mean grain size: 0.05-0.1 μm) was taken, centrifuged and washed twice to obtain a microsphere precipitate, and the obtained microsphere template was for further use;

(3) 5 mL silk fibroin solution obtained in the step (1) was blended with the microsphere template in the step (2), after being blown evenly, subjected to ultrasonic dispersion for 10 min, and placed at 4° C. for reaction for 15 min;

(4) 2 μL aminopropyl triethoxysilane was added to the reaction solution in the step (3), and shaken vigorously for 5 s, then placed at 4° C. for reaction for 15 min;

(5) the reaction system obtained in the step (4) was centrifuged at 15000 rpm for 15 min to remove supernatant, and washed with deionized water twice to obtain a precipitate;

(6) 5 mL silk fibroin was added to the precipitate in the step (5) again and the reaction steps of (3)-(5) were repeated for 5 times, and silk fibroin was used for the final treatment only to obtain a silk fibroin coated polystyrene composite; the total number of silk fibroin coating layers was 6. After through potential test, the surface potential is negative and surface potential variation is shown in FIG. 1;

(7) the product in the step (6) was treated with 5 mL dimethyl formamide for 24 h to remove the polystyrene template; centrifuged and washed to obtain a hollow drug-loaded silk fibroin nanocapsule. The SEM morphology is shown in FIG. 2; and (8) the drug-loaded silk fibroin nanocapsule was co-cultured with an antitumor drug with a positive potential, doxorubicin hydrochloride for 24 h to load the drug.

Example 2

(1) Silkworm silk fibroin was extracted and a concentration of the silk fibroin was regulated to be 2 mg/mL for further use;

(2) 0.5 mL polystyrene microsphere solution after being treated by surface carboxylation (—COOH) (Aladdin, carboxyl polystyrene microsphere, concentration: 25 g/L, and microsphere mean grain size: 0.05-0.1 μm) was taken, centrifuged and washed twice to obtain a microsphere precipitate;

(3) the microspheres were dispersed with 5 mL deionized water once again, and 2 μL aminopropyl triethoxysilane was added, and shaken vigorously for 5 s, then placed at 4° C. for reaction for 15 min;

(4) the reaction solution in the step (3) was centrifuged to remove supernatant, then 5 mL silk fibroin was added and blown evenly, and subjected to ultrasonic dispersion for 10 min, and placed at 4° C. for reaction for 15 min;

(5) 2 μL aminopropyl triethoxysilane was added to the reaction solution in the step (4) again, and shaken vigorously for 5 s, then placed at 4° C. for reaction for 15 min;

(6) the reaction system obtained in the step (5) was centrifuged at 12000 rpm for 15 min to remove supernatant, and washed with deionized water twice to obtain a precipitate;

(7) the reaction steps of (4)-(6) were repeated for 8 times, and APTES (aminopropyl triethoxysilane) was used for the final treatment only to obtain a silk fibroin coated polystyrene composite; the total number of silk fibroin coating layers was 9; after through potential test, the surface potential was negative;

(8) the product in the step (7) was treated with 8 mL dimethyl formamide for 24 h to remove the polystyrene template; centrifuged and washed to obtain a hollow drug-loaded silk fibroin nanocapsule; and (9) the drug-loaded silk fibroin nanocapsule was co-cultured with a plasmid with a negative potential for 24 h such that the plasmid was loaded and delivered inside the cells for gene therapy.

Example 3

(1) Silkworm silk fibroin was extracted and a concentration of the silk fibroin was regulated to be 1 mg/mL for further use;

(2) 1 mL surface-aminated (—$NH_2$) polystyrene microsphere solution (Aladdin, amino polystyrene microsphere, concentration: 25 g/L, and microsphere mean grain size: 0.1-0.2 μm) was taken, centrifuged and washed twice to obtain a microsphere precipitate;

(3) the 5 mL silk fibroin solution was blended with the microsphere template in the step (2), after being blown evenly, subjected to ultrasonic dispersion for 10 min, and placed at 4° C. for reaction for 15 min;

(4) 5 μL aminopropyl triethoxysilane was added to the reaction solution in the step (3), and shaken vigorously for 5 s, then placed at 4° C. for reaction for 15 min;

(5) the reaction system obtained in the step (4) was centrifuged at 12000 rpm for 15 min to remove supernatant, and washed with deionized water twice to obtain a precipitate;

(6) 5 mL silk fibroin was added to the step (5) again and the reaction steps of (3)-(5) were repeated for 8 times to obtain a silk fibroin coated polystyrene composite; the total number of silk fibroin coating layers was 9; after through potential test, the surface potential was negative; and (7) the product in the step (6) was treated with 10 mL dimethyl formamide for 24 h to remove the polystyrene template, centrifuged and washed to obtain a drug-loaded silk fibroin nanocapsule with a thicker shell.

Figure 3:
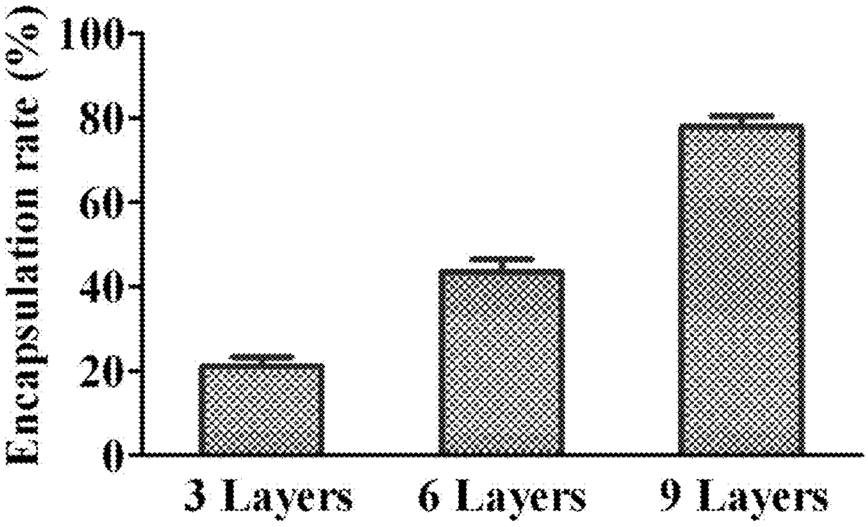
FIG. 3 shows a loading rate diagram of a fibroin microcapsule drug in Example 3.

A 3-layered drug-loaded silk fibroin nanocapsule was prepared according to the method of Example 1. Afterwards, the 3-layered drug-loaded silk fibroin nanocapsule, the drug-loaded silk fibroin nanocapsule prepared in Example 1 and the drug-loaded silk fibroin nanocapsule prepared in Example 3 were co-cultured with an antitumor drug with a positive potential, doxorubicin hydrochloride for 24 h, capable of loading the drug. The drug loading rate is shown in FIG. 3; as shown in FIG. 3, the 9-layered drug-loaded silk fibroin nanocapsule has a loading rate of 80% above.

Finally, it should be noted that the above examples are merely detailed embodiments of the present invention. Apparently, the present invention is not limited to the above examples. Further, there are lots of transformations. A person skilled in the art can directly derive or associate with all the transformations from the disclosure of the present invention. Moreover, these transformations shall be regarded within the protection scope of the present invention.

What is claimed:

1. A method for preparing a hollow silk fibroin nanocapsule used for drug-loading, comprising:

performing a coating treatment of applying alternating layers of silk fibroin and 3-aminopropyl triethoxysilane on functionally modified polystyrene spheres having a diameter of 0.05-0.1 μm, to ultimately obtain a multilayer coated polystyrene composite with a negative or positive surface potential, and finally removing the functionally modified polystyrene spheres with a template-removing reagent, to obtain a hollow silk fibroin nanocapsule, wherein 3-aminopropyl triethoxysilane is a cross-linking agent to bind and induce silk fibroin to be coated alternatively, thereby forming layer-by-layer assembly, wherein, when the functionally modified polystyrene spheres are positive potential spheres, silk fibroin is used for a first coating; and in the case of negative potential spheres, 3-aminopropyl triethoxysilane is used for the first treatment, wherein the functionally modified polystyrene spheres comprise an amination surface modification for positive surface potential or a carboxylation surface modification for negative surface potential, and wherein when loading a molecule drug with positive potential, a hollow silk fibroin nanocapsule characterized with negative surface potential from a final coating treatment with silk fibroin is used, when loading a negative potential molecule drug, a hollow silk fibroin nanocapsule characterized with positive surface potential from the final coating treatment with 3-aminopropyl triethoxysilane is used.

2. The method for preparing a hollow silk fibroin nanocapsule used for drug-loading according to claim 1, characterized in that the step of performing the coating treatment by silk fibroin is as follows: adding the to-be-coated polystyrene spheres into a silk fibroin aqueous solution followed by ultrasonic dispersion, then transferring the dispersed solution to a low temperature environment at 0-10° C. for continuous reaction, after 5-50 min, the first coating is completed, wherein the silk fibroin aqueous solution used here has a concentration of 1-10 mg/mL.

3. The method for preparing a hollow silk fibroin nanocapsule used for drug-loading according to claim 1, characterized in that the step of performing the coating treatment by 3-aminopropyl triethoxysilane is as follows: mixing the to-be-coated polystyrene spheres with 3-aminopropyl triethoxysilane in a solvent evenly, and then transferring the dispersed solution to a low temperature environment at 0-10° C. for continuous reaction for 5-50 min to complete the reaction, and removing the solvent to complete the coating.

4. The method for preparing a hollow silk fibroin nanocapsule used for drug-loading according to claim 1, characterized in that the spheres with final coating layer of silk fibroin carry a negative potential on the outermost surfaces, and the 3-aminopropyl triethoxysilane finally-coated spheres carry a positive potential on the outermost surfaces.

5. The method for preparing a hollow silk fibroin nanocapsule used for drug-loading according to claim 1, characterized in that directed to 10 mg functionally modified polystyrene spheres, the required silk fibroin has a mass of 1-20 mg for each silk fibroin coating treatment, the required 3-aminopropyl triethoxysilane has a mass of 1-5 mg for each 3-aminopropyl triethoxysilane coating treatment.

6. The method for preparing a hollow silk fibroin nanocapsule used for drug-loading according to claim 1, characterized in that alternatively coating silk fibroin and 3-aminopropyl triethoxysilane once respectively is termed as one layer and there are total 3-15 layers.

7. A hollow silk fibroin nanocapsule used for drug-loading, characterized in that the hollow silk fibroin nanocapsule is prepared by a method comprising:

performing a coating treatment of applying alternating layers of silk fibroin and 3-aminopropyl triethoxysilane on functionally modified polystyrene spheres having a diameter of 0.05-0.1 μm, to ultimately obtain a multilayer coated polystyrene composite with a negative or positive surface potential, and finally removing the functionally modified polystyrene spheres with a template-removing reagent, to obtain a hollow silk fibroin nanocapsule, wherein the 3-aminopropyl triethoxysilane is a cross-linking agent to bind and induce silk fibroin to be coated alternatively, thereby forming layer-by-layer assembly, wherein, when the functionally modified polystyrene spheres are positive potential, silk fibroin is used for a first coating, and in the case of negative potential spheres, 3-aminopropyl triethoxysilane is used for the first treatment, wherein the functionally modified polystyrene spheres comprise an amination surface modification for positive potential or a carboxylation surface modification for negative potential, and wherein when loading a molecule drug with positive potential, a hollow silk fibroin nanocapsule characterized with negative surface potential from the final coating treatment with silk fibroin is used, when loading a negative potential molecule drug, a hollow silk fibroin nanocapsule characterized with positive surface potential from the final coating treatment with 3-aminopropyl triethoxysilane is used.

8. The method for preparing a hollow silk fibroin nanocapsule used for drug-loading according to claim 1, wherein the template-removing reagent is dimethyl formamide.

* * * * *